United States Patent
Ji

(10) Patent No.: US 6,740,502 B2
(45) Date of Patent: May 25, 2004

(54) METHOD FOR PREPARING ZINC-OLIGOPEPTIDE EASILY ABSORBABLE BY THE HUMAN BODY

(76) Inventor: Sung Kyu Ji, 83-8, Nonhyun-dong, Kangnam-ku, Seoul 135-010 (KR)

( * ) Notice: Subject to any disclaimer, the term of this patent is extended or adjusted under 35 U.S.C. 154(b) by 182 days.

(21) Appl. No.: 09/730,542

(22) Filed: Dec. 7, 2000

(65) Prior Publication Data

US 2002/0028769 A1 Mar. 7, 2002

(30) Foreign Application Priority Data

Jul. 11, 2000 (KR) .................................. 2000-39595

(51) Int. Cl.[7] .................................................. C12P 21/06
(52) U.S. Cl. ...................................................... 435/68.1
(58) Field of Search ............................ 435/68.1; 424/439, 424/400; 426/72

(56) References Cited

U.S. PATENT DOCUMENTS

| | | | | | |
|---|---|---|---|---|---|
| 3,969,540 | A | * | 7/1976 | Jensen | ..................... 426/657 |
| 4,020,158 | A | * | 4/1977 | Ashmead et al. | ............. 514/6 |
| 4,076,803 | A | * | 2/1978 | Ashmead | ..................... 514/6 |
| 4,172,072 | A | * | 10/1979 | Ashmead | ..................... 435/272 |
| 4,201,793 | A | * | 5/1980 | Ashmead | ..................... 426/271 |
| 4,216,143 | A | * | 8/1980 | Ashmead | ..................... 426/656 |
| 4,599,152 | A | * | 7/1986 | Ashmead | ..................... 205/435 |
| 4,774,089 | A | * | 9/1988 | Ashmead | ..................... 424/679 |
| 4,830,716 | A | * | 5/1989 | Ashmead | ..................... 205/435 |
| 5,292,538 | A | * | 3/1994 | Paul et al. | ..................... 426/271 |
| 5,516,925 | A | * | 5/1996 | Pedersen et al. | ............. 556/116 |
| 5,997,908 | A | * | 12/1999 | Song | |
| 6,166,071 | A | * | 12/2000 | Ashmead et al. | ............. 426/74 |

* cited by examiner

*Primary Examiner*—Jon P. Weber
(74) *Attorney, Agent, or Firm*—Birch, Stewart, Kolasch & Birch, LLP

(57) ABSTRACT

Disclosed is a method for preparing zinc-oligopeptides easily absorbable by the human body. A suspension of protein in deionized water at a neutral pH range in the presence of a protease is subjected to proteolysis to give a mixture of oligopeptides. Zinc ions are chelated with the oligopeptides to give a zinc-oligopeptide solution. The zinc-oligopeptide solution is concentrated and dried to a powder. Also provided is a beverage or food composition containing the zinc-oligopeptide, which can make contribution to avoid the lack of dietary zinc.

3 Claims, 2 Drawing Sheets

Zinc-Oligopeptide

Zinc-Oligopeptide

METHOD FOR PREPARING ZINC-OLIGOPEPTIDE EASILY ABSORBABLE BY THE HUMAN BODY

BACKGROUND OF THE INVENTION

The present invention relates to a method for preparing zinc-oligopeptides which can be easily absorbed by the human body. Also, the present invention is concerned with a beverage or food composition, which can easily provide zinc for the human body.

Loss of the mineral balance in the body has been found as one of the causes of adult diseases, which have recently been increasing in incidence. With growing older, the human body becomes poorer at absorbing minerals. Nowadays, a deluge of processed foods is becoming as one main cause of upsetting the mineral balance of the body because most of them contain materials inhibiting mineral absorption.

Of various minerals, zinc is involved particularly in the onset of diabetes mellitus, one of the most popular diseases today. In fact, not only adults, but also a surprising number of children suffer from the disease at present, which is believed to be attributed in part to the lack of zinc. In Oriental medicine, zinc is also described to have physiological activity associated with sugar control and vigor in the body. Deeply affected in diabetes mellitus patients, the blood sugar control of the body has direct influence on the energy production necessary for life. Although other physiological functions are active, abnormal regulation of blood sugar in the body, which means that the metabolic process of converting sugar into energy is in an abnormal state, lowers the immunity of the body to exogenous pathogens as well as latent viruses, resulting in the body falling ill.

In the body, zinc serves as an essential mineral in activating insulin, in addition to being involved in regenerating muscle tissues and nerve tissues. Abundant as it is in blood, insulin cannot exert its full effects in the absence of zinc. That is, insulin which is not associated with zinc is not beneficial to diabetics. A similar case can be found with amylase, which is unable to function as a saccharification catalyst unless it is associated with ionic calcium.

One of the most important physiological activities of zinc is to activate insulin into a form useful in the treatment of diabetes mellitus. In turn, the activated insulin is responsible, in great part, for the production of energy. In addition, zinc was found to inhibit the expression of mutant genes, thereby making a contribution to anticancer activity. Further, zinc is known to take part in a catalytic reaction necessary for DNA polymerization and therefore affect the rapid regeneration of injured tissue. In this regard, zinc has some connection with acceleration of wound healing, prevention of prostate problems and hair loss, and treatment of acne and rheumatoid arthritis.

Recently, sufficient intake of zinc has been reported to significantly decrease the incidence of disease in children. When their diets are supplemented with zinc, children are 40% less likely to be taken ill with pneumonia and 25% less likely to get diarrhea. As stated above, diabetes mellitus may be caused when dietary zinc is insufficient. When insulin is not activated, the body is significantly deprived of available sugar, leading to loss of vigor.

In order to be activated in association with zinc, the insulin must not be in a pro-insulin form, but in a functional form. Stoichiometrically, one molecule of functional insulin (molecular weight 6,615) associates with a zinc atom (atomic weight 65). Therefore, functional insulin must be associated with zinc at a weight ratio of approximately 1,000:1. In the medical world, globulin zinc I is used as an insulin formulation, which is generally for subcutaneous injection, for the purpose of zinc activation of insulin.

Occurrence of diabetes mellitus in children in recent times, which was rare in the past, is believed to be strongly affected by dietary lifestyles, but not heredity. Fried foods, which children usually like, contain a large quantity of fat that suppresses the activity of zinc. Also, a high intake of processed foods inhibits activities of calcium as well as zinc because of their high contents of phosphoric acid. Lipids and phosphates are known to actively inhibit the absorption of minerals irrespective of which form they have.

Naturally, living bodies have to supplement consumed or deficient materials by themselves. Hence, it is necessary that people exercise restraint in their ingestion of materials which inhibit such a natural supplementary function. The loss of the supplementary functions owing to ingestion of inhibitory materials causes a vicious cycle of deficiency. For instance, deficient dietary zinc lowers the activity of insulin, and unconsumed insulin causes a decrease or ceasing of the production of insulin in the pancreas. On the other hand, when insulin is actively consumed, it must be replaced, and thus insulin is more actively produced in the pancreas. This is demonstrated by the fact that athletes, who consume large energy, contain zinc at an amount 20 times as much as that of ordinary people. Zinc enables insulin to actively promote the metabolism of sugar in the body.

However, most of the mineral-enriched materials developed thus far, are poor in absorbability by the human body. Calmodulin, a calcium-chelated oligopeptide, was found in neurotic system of the human body, and to be absorbed easy as Calmodlin molecular structure by the small intestine.

SUMMARY OF THE INVENTION

Hinted by the structure of calmodulin, the intensive and thorough research on facilitating of the human body to absorb zinc, conducted by the present inventors, resulted in the finding that minerals are better absorbed by the body when they combine with organic materials, especially oligopeptides, rather than alone.

Therefore, it is an object of the present invention to provide a method for preparing a zinc-oligopeptide which can be easily absorbed by the body.

It is another object of the present invention to provide use of zinc-oligopeptide in foods.

In accordance with an aspect of the present invention, there is provided a method for preparing a zinc-oligopeptide easily absorbable by the body, comprising the steps of: proteolyzing a suspension of protein in deionized water at a neutral pH range in the presence of a protease to give a mixture of oligopeptides; chelating zinc ions with the oligopeptides to give a zinc-oligopeptide solution; concentrating the zinc-oligopeptide solution and drying the concentrate to a powder.

In accordance with another aspect of the present invention, there is provided a beverage comprising the zinc-oligopeptide, in combination with at least one ingredient selected from the group consisting of vitamin-C, vitamin-$B_1$, vitamin-$B_2$, fructose, α-amylase decomposed starch and magnesium stearate.

DETAILED DESCRIPTION OF THE INVENTION

Figure 1:
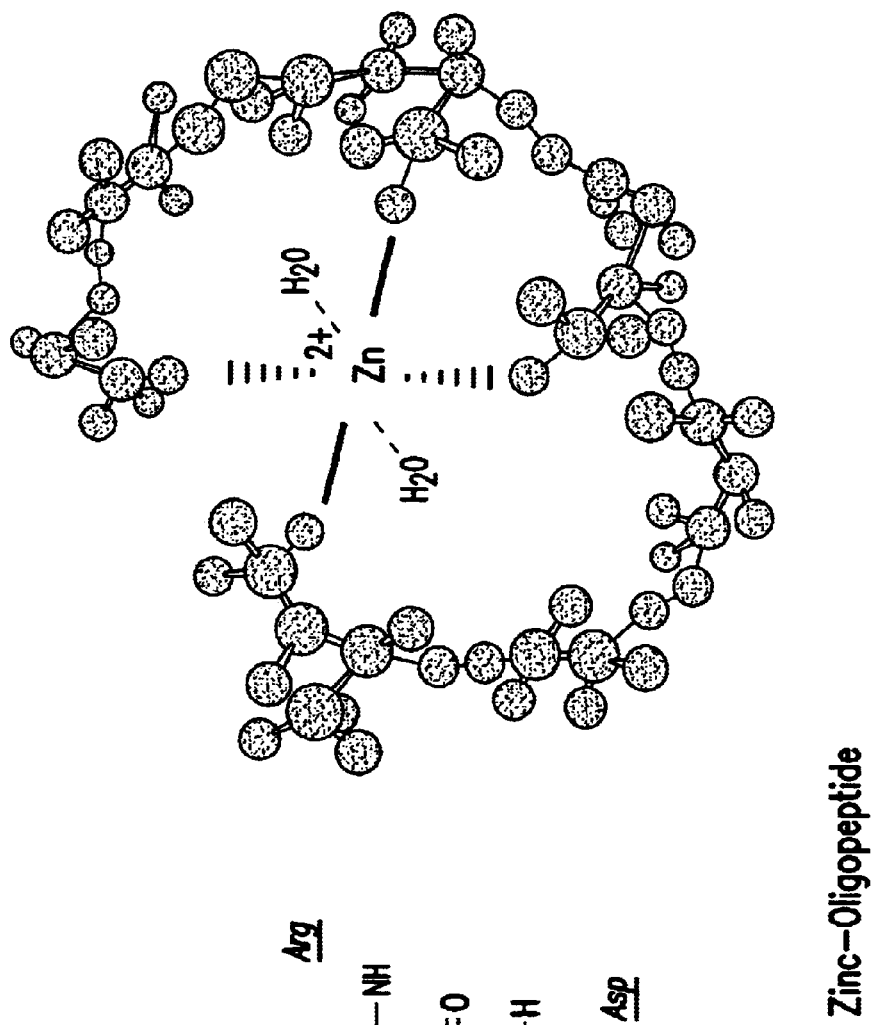
FIG. 1 shows a structure of an oligopeptide associated with a zinc ion.
Figure 1:
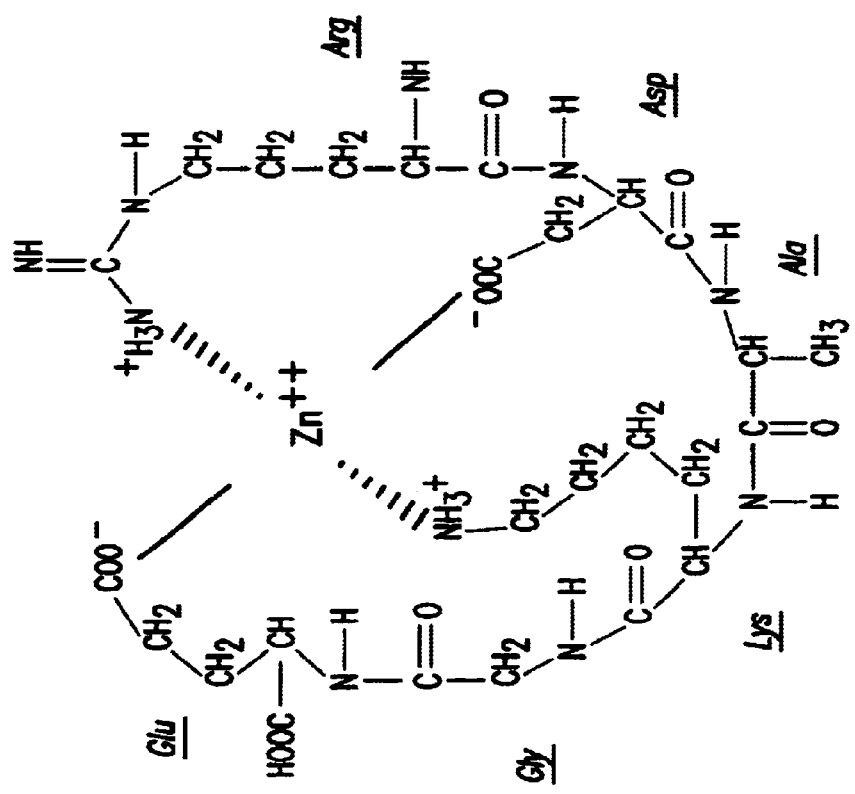
Figure 2:
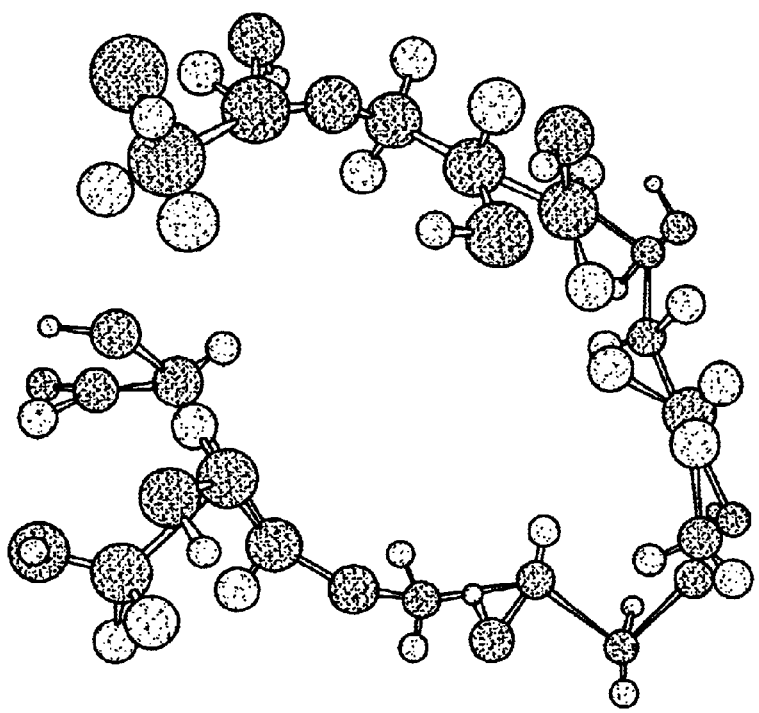
FIG. 2 shows a structure of an oligopeptide alone.
Figure 2:
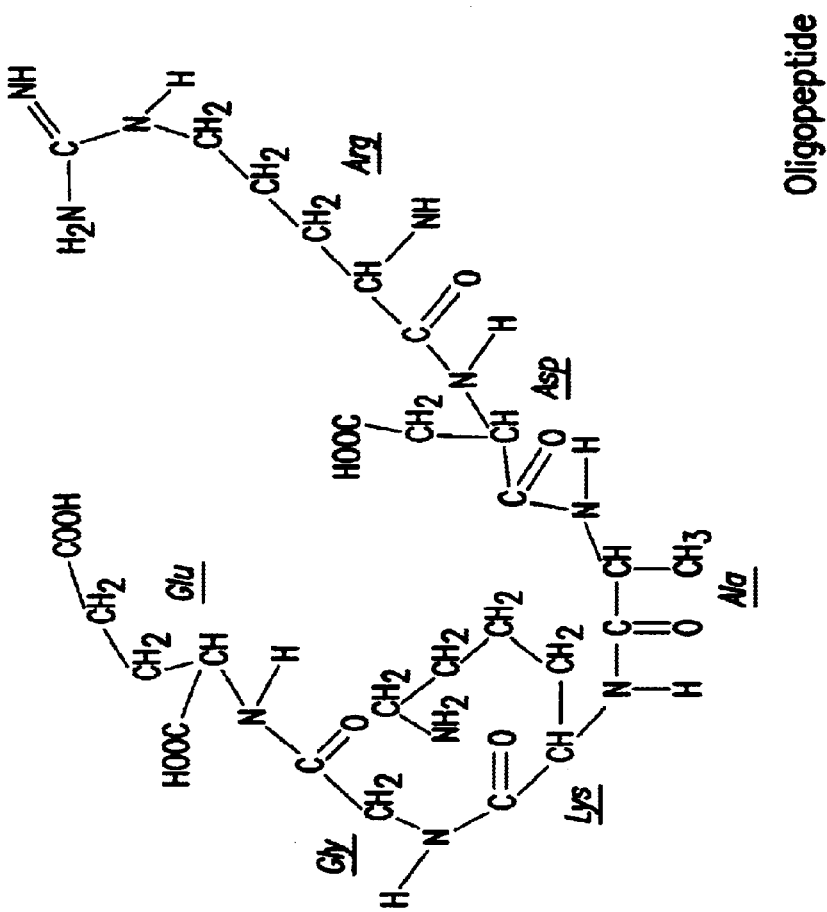

In accordance with one embodiment of the present invention, there is provided a method for preparing zinc-oligopeptide. First, a suspension of protein in deionized water is subjected to proteolysis in a neutral pH range for a long period of time to give oligopeptides. These are used to chelate zinc ions to form zinc-oligopeptides. The resulting solution is concentrated and dried to yield zinc-oligopeptide powder.

In detail, 100 weight parts of protein are suspended in 800 weight parts of deionized water and added with 2–4 weight parts of protease. Proteolytic reaction is conducted at pH 3.5–6.0 for 10–12 hours to give oligopeptides. Based on 1,000 weight parts of the oligopeptide thus obtained, one weight part of zinc ions is mixed and allowed to chelate, to yield a zinc-oligopeptide. Then, the resulting zinc-oligopeptide solution is concentrated to a solid content of 32–36% and dried to produce zinc-oligopeptide powder.

Either vegetable protein or animal protein may be used for obtaining oligopeptides.

In accordance with another embodiment of the present invention, there is provided a zinc-oligopeptide-containing beverage. To this end, vitamin-C, vitamin-$B_1$, vitamin-$B_2$, fructose, α-amylase decomposed starch, and/or magnesium stearate may be mixed with liquid zinc-oligopeptide. Alternatively, this composition is dehydrated to give powder suitable for use in capsules or tablets.

More specifically, 99.5% of the zinc-oligopeptide is mixed with 0.01–0.05% of vitamin-C, 0.01–0.05% of vitamin-$B_1$, 0.01–0.05% of vitamin-$B_2$, 4.0–5.0% of α-amylase decomposed starch, and/or 0.01–0.05% of magnesium stearate.

A better understanding of the present invention may be obtained in light of the following examples which are set forth to illustrate, but are not to be construed to limit the present invention.

EXAMPLE 1

As an oligopeptide source, a vegetable protein such as bean protein and gluten, or an animal protein such as casein and gelatin was used. 100 weight parts of protein with a purity of 95% or higher was suspended in 800 weight parts of water and allowed to undergo proteolysis in the presence of 3 weight parts of protease at pH 3.5–6.0 for 12 hours to give oligopeptides. Of the proteolysates, non-water soluble ones were filtered off. One weight part of zinc ions was added based on 1,000 weight parts of the oligopeptide to form a zinc-oligopeptide composite. Then, the resulting solution was concentrated to a solid content of 35% and spray-dried to give a zinc-oligopeptide powder.

EXAMPLE 2

The zinc-oligopeptide solution prepared in Example 1 was controlled to have a concentration of 28% and formulated as indicated in Table 1, below, to provide a zinc-oligopeptide beverage with a full recommended dietary allowance (RDA) of zinc (12–15 mg/day).

TABLE 1

Composition of Zinc-Oligopeptide Beverage

| Ingredients | Amounts (wt %) |
| --- | --- |
| 28% Zn-Oligopeptide Sol'n | 1.0 |
| Vitamin-$B_1$ | 0.01 |
| Fructose | 12 |
| Vitamin-C | 0.03 |
| Vitamin-$B_2$ | 0.01 |
| Water | 86.95 |
| Total | 100 |

EXAMPLE 3

The zinc-oligopeptide prepared in Example 1 was formulated with other ingredients as shown in Table 2, below, and 0.5 g of the resulting mixture was filled into a capsule.

TABLE 2

Composition of Zinc-Enriched Capsule

| Ingredients | Amounts (wt %) |
| --- | --- |
| Zn-Oligopeptide Powder | 99.95 |
| Vitamin-$B_1$ | 0.01 |
| Vitamin-C | 0.03 |
| Vitamin-$B_2$ | 0.01 |
| Total | 100 |

EXAMPLE 4

The zinc-oligopeptide prepared in Example 1 was formulated with other ingredients as shown in Table 3, below, and 0.5 g of the resulting mixture was formed into a zinc-enriched tablet.

TABLE 3

Composition of Zn-Enriched Tablet

| Ingredients | Amounts (wt %) |
| --- | --- |
| Zn-Oligopeptide Powder | 94.95 |
| Vitamin-$B_1$ | 0.01 |
| α-Amylase Decomposed starch | 4.7 |
| Vitamin-C | 0.03 |
| Vitamin-$B_2$ | 0.01 |
| Mg Stearate | 0.3 |
| Total | 100 |

As described hereinbefore, the zinc-oligopeptide of the present invention has a molecular weight of from 800 to 1,000. Because its molecular weight is smaller than the average molecular weight (24,000–28,000) of membrane integral proteins of the small intestine, through which molecules pass in and out of the cell, the zinc oligopeptide of the present invention can be readily absorbed by the body. Additionally, zinc is chelated by water-soluble oligopeptides, so that its absorption by the body is not inhibited by other compounds present in the digestive tract.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing a zinc-oligopeptide easily absorbable by the body, comprising the steps of:

proteolyzing a suspension of protein in deionized water at a neutral pH range in the presence of a protease to give a mixture of oligopeptides;

chelating zinc ions with the oligopeptides to give a zinc-oligopeptide solution;

concentrating the zinc-oligopeptide solution and drying the concentrate to a powder;

wherein the zinc-oligopeptide possesses a structure as shown in FIG. 1.

2. A method of preparing a zinc-oligopeptide easily absorbable by the body, comprising the steps of:

preparing a suspension of protein by suspending 100 parts by weight of protein in 800 parts by weight of deionized water, proteolyzing the protein suspension at pH 3.5–6.0 for 10–12 hours in deionized water in the presence of 2–4 parts by weight of protease to give a mixture of oligopeptides, chelating zinc ions with the mixture of oligopeptides in a weight ratio of zinc/oligopeptdes of 1/1,000 to yield a zinc-oligopeptide solution, and concentrating the zinc-oligopeptide solution to a solid content of 32–36% and drying to produce a zinc-oligopeptide powder;

wherein the zinc-oligopeptide possesses a structure as shown in FIG. 1.

3. The method as set forth in claim 1, wherein the protein is an animal protein or a vegetable protein.

* * * * *